United States Patent [19]

von Buenau

[11] 4,213,147
[45] Jul. 15, 1980

[54] SYSTEM FOR BUILD-UP AND REPRODUCTION OF ULTRASONIC IMAGES ON REPRODUCTION MEDIA

[75] Inventor: Heinrich von Buenau, Erlangen, Fed. Rep. of Germany

[73] Assignee: Siemens Aktiengesellschaft, Berlin & Munich, Fed. Rep. of Germany

[21] Appl. No.: 834,914

[22] Filed: Sep. 20, 1977

[30] Foreign Application Priority Data

Sep. 30, 1976 [DE] Fed. Rep. of Germany ....... 2644190

[51] Int. Cl.$^2$ .............................................. H04N 7/18
[52] U.S. Cl. .................................... 358/112; 358/139
[58] Field of Search ................. 358/10, 139, 112, 169; 324/20 R, 20 CR; 73/18; 340/1 R

[56] References Cited

U.S. PATENT DOCUMENTS

| | | | |
|---|---|---|---|
| 2,763,833 | 9/1956 | Brumbaugh | 358/139 |
| 2,801,385 | 7/1957 | Bendell | 358/139 |
| 2,885,470 | 5/1959 | Bartelink | 358/139 |
| 2,911,466 | 11/1959 | Greenhead | 358/139 |
| 3,996,420 | 12/1976 | Geluk | 358/169 |
| 4,058,001 | 11/1977 | Waxman | 358/112 |

OTHER PUBLICATIONS

Cordesses et al.-A Display System for an Acoustic Radar IEEE Transactions on Geoscience Electronics-vol. GE-12, #4 (1974), pp. 140-145.

*Primary Examiner*—Robert L. Griffin
*Assistant Examiner*—Joseph A. Orsino, Jr.
*Attorney, Agent, or Firm*—Hill, Van Santen, Steadman, Chiara & Simpson

[57] ABSTRACT

In an illustrated embodiment, ultrasonic image processing equipment of the B scan type selectively supplies successive lines of an ultrasonic image signal to a signal mixer which also may receive a gray scale signal. Each successive ultrasonic field interval may thus have inserted therein a gray scale signal so that the ultrasonic display oscilloscope shows a flicker-free gray scale at one margin of the ultrasonic image display area, extending parallel to the line sweep direction (depth direction). By subjecting the gray scale signal to the video standards conversion and to the other transmission processes, e.g. photoelectric and photochemical conversion processes, used in video display and documentation, it is possible to prevent the loss of medically relevant information in these processes. The gray scale signal line or lines may alternate with the ultrasonic lines in each field interval so as to be recorded on magnetic tape, motion picture film and other media along with each ultrasonic image field.

6 Claims, 1 Drawing Figure

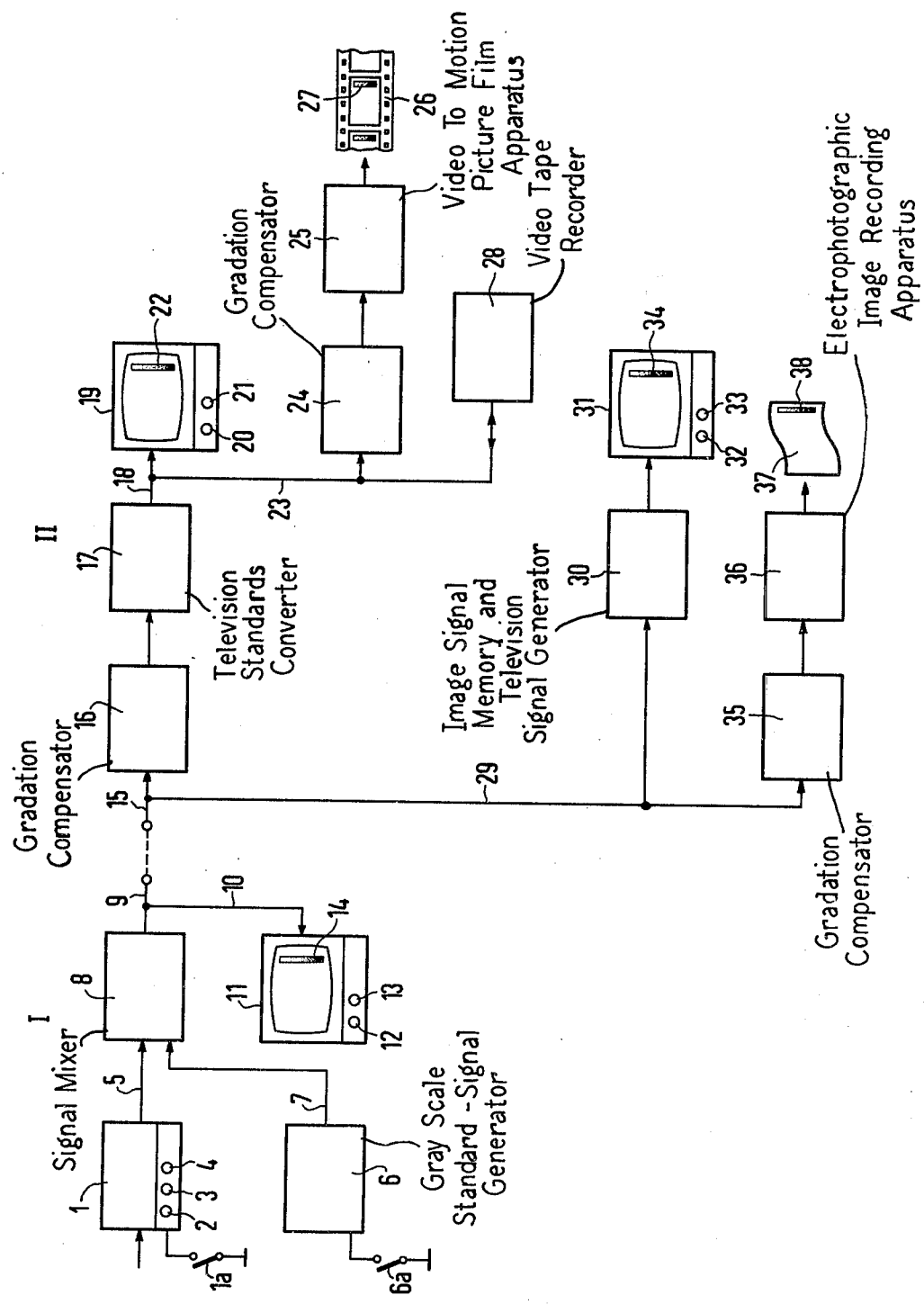

SYSTEM FOR BUILD-UP AND REPRODUCTION OF ULTRASONIC IMAGES ON REPRODUCTION MEDIA

BACKGROUND OF THE INVENTION

The invention relates to a system for the build-up and reproduction of ultrasonic images on reproduction media comprising at least one reproduction apparatus connected to an image signal processing apparatus to which the image signal produced by an ultrasonic transducer through scanning of an ultrasonographic subject is conveyed for the purpose of image build-up, and which possesses adjustment means which can be actuated manually for the free parameters of the image signal being issued, such as e.g. initial amplification, depth compensation, and dynamic compression.

In ultrasonography, it is frequently desirable to convey the primary ultrasonic image built up on the ultrasonic imaging apparatus to additional reproduction apparatus for example, television monitors, for the purpose of viewing and/or to transfer said primary ultrasonic image to documentation in the form of a magnetic tape, film, or paper image. For this purpose, it is fundamentally possible to transmit via a standards converter, the ultrasonic image from the ultrasonic imaging apparatus to a television monitor, convey it to a video recorder and produce a film, or individual paper images, respectively, by means of image recording apparatus. However, it has been shown that secondary pictures of this type do not achieve the quality of the primary ultrasonic image. In the case of the known systems for the purpose of ultrasonic image production, the operator adjusts the image on the ultrasonic imaging apparatus such that the image contents are capable of being diagnostically optimally evaluated. In order to effect this adjustment, the free parameters of the apparatus for image signal processing, such as e.g. initial amplification, depth compensation, and volume (or dynamic) compression, can be systematically varied. However, since the image build-up—particularly for the purpose of response to medical interrogation—is also dependent upon influencing factors which can only be subjectively determined by the operator, including, e.g., the ambient luminance of the room, the ultrasonic image is not capable of being clearly reproduced in the conventional manner by means of a transmission chain as is the case in television technology, for example. In television transmission chains, a standard signal—e.g. a test image—is directly fed into the video signal line by the television camera (vidicon). However, this is not possible in the case of sonographic image representation, since the ultrasonic image must first be built-up, independently of the image transmission, on the reproduction apparatus; e.g., an oscilloscope which is connected to the image signal processing apparatus. For this reason, an attempt was made to achieve a conditioning of the sonographic transmission path with the aid of the ultrasonic image itself which was to be transmitted and diagnostically evaluated. However, attempts of this sort led to purely fortuitous results and were therefore unsatisfactory in the end.

SUMMARY OF THE INVENTION

Accordingly, it is the object of the invention to produce a system for the build-up and reproduction of ultrasonic images on reproduction media wherein the image to be diagnostically evaluated is transmitted to the reproduction media in a defined, controllable, and reproduceable fashion.

In accordance with the invention, the object is achieved by virtue of the fact that there is provided between the image signal processing apparatus and the reproduction apparatus a signal mixer for the purpose of feeding a gray scale value-standard signal from a standard-signal generator into the image signal-transmission path. Preferably, a gray scale signal with a defined black-white gradation is employed as the standard signal. In accordance with the inventive procedure for operation of the system, in order to prevent the loss of diagnostically relevant image contents, a first method step specifies that by fading in a gray scale value-standard signal, the reproduction apparatus is adjusted to optimum reproduction properties of contrast and gradation with a set of regulatory devices, preferably for brightness and contrast, and, in a second method step, the image to be diagnostically evaluated is built-up on the reproduction apparatus with the use of the adjustment means of the image signal processing apparatus, preferably for initial amplification, depth compensation, and volume (or dynamic) compression. By adjusting the additional reproduction apparatus and image recording apparatus according to contrast and gradation with the aid of the gray scale value-standard signal, an optimum reproduction of the image to be diagnostically evaluated is simultaneously achieved.

The invention was preceded by a detailed problem-analysis whose aim was to seek out the reasons for the unsatisfactory image transmission properties in sonography utilizing known transmission chains: From a purely technical point of view, the ultrasonic image produced on a monitor with the image signal processing unit can be described solely by its image points and their luminous intensity. However, since the human eye judges brightness and contrast according to the ambient luminance of the room and according to the image size, it is possible for errors to occur even in the case of identical transmission of photometric image contents from a first reproduction medium to a following reproduction medium. In addition, in a transmission chain, the luminous intensity information of the individual point passes through photoelectric or photochemical conversion processes. In general, such processes are not linear. Particularly where several conversions are superimposed, consequent gradation errors occur which are no longer controllable.

These cited sources of error lead to a loss of image contents which also carry medical information. In accordance with the invention, a loss of information is largely prevented. A transmission chain operated with the inventive system and the inventive procedure provides optimum ultrasonic images and image-reproductions, since the transmission properties are clearly defined. If a gray scale with a defined black-white-gradation is employed as the standard signal, an optimum reproduction of the entire image contents is effected by means of an optimum reproduction of the gray scale signal prior to the actual build-up of the ultrasonic image. This is controllable in a simple fashion.

Other objects, features and advantages of the present invention will be apparent from the following detailed description taken in connection with the accompanying sheet of drawings.

BRIEF DESCRIPTION OF THE DRAWINGS

The single FIGURE of drawings illustrates in the form of a block diagram a basic system for the build-up and reproduction of ultrasonic images on reproduction media, in accordance with the present invention.

DETAILED DESCRIPTION OF A PREFERRED EMBODIMENT

In the FIGURE, I designates the primary region at the ultrasonic apparatus for the operator, and II designates the secondary region for the additional viewers, or for the image recording, respectively. These two regions are interconnected via signal lines or in a wireless fashion.

In the FIGURE, 1 designates the apparatus for processing an ultrasonic image signal. With the latter, the image signals emitted by the ultrasonic transducer are build-up into an image, whereby the free parameters: initial amplification, depth compensation, and volume (or dynamic) compression, are adjustable by the operator at regulating devices 2, 3, and 4. By means of switch 1a apparatus 1 can be switched on or off. Reference numeral 5 designates the output line of the apparatus for image signal processing 1, which output line carries the entire image information. A gray scale value standard in the form of a gray scale is fed-in via line 7 from standard-signal generator 6. The standard-signal generator can be switched on or off via switch 6a. Lines 5 and 7 lead to the signal mixer 8 in which the image signal and the gray scale value signal are mixed with a defined coupling. Via line 9 the common signal information is conducted from primary region I to secondary region II. The image information is delivered to monitor 11 via return line 10. Monitor 11 thereby functions as control apparatus for the operator as well as the primary reproduction apparatus for the viewer. Contrast and brightness are adjustable as free parameters on monitor 11 by regulating devices 12 and 13.

Secondary region II consists of the diverse reproduction media: In the sample embodiment, the ultrasonic image is to be optionally represented on an additional television monitor, stored on a video recorder, and/or further processed in the form of a film or an individual picture. For this purpose, the total signal information received in secondary region II is conveyed via line 15 to a processing line which consists of an apparatus for gradation compensation 16 (screen/television camera) and a television standards converter 17 which, by means of a television camera (vidicon), converts the ultrasonic image from the recording standard of the primary monitor 11 to a standard suitable for television. The video signal information delivered by standards converter 17 is then present on line 18 in the CCIR-standard, and is delivered to television monitor 19 wherein brightness and contrast are variable as free parameters by means of regulating devices 20 and 21 and are controllable by means of the gray scale signal 22. Via line 23, an apparatus for gradation compensation 24 (screen/film) for a following CINE-converter 25 is parallel-connected. In CINE-converter 25, a conventional narrow-gauge film 26 is produced, on the individual images of which the gray scale 27 is visible, respectively. In addition, there is parallel-connected to television monitor 19 a video recorder 28 through which the television image is stored on tape, or played off from the tape to television monitor 19, respectively.

For a purely electronic image processing (for individual pictures), the secondary input signal is delivered in an analogous fashion to a signal memory and transducer 30 via line 29 which is connected in parallel with line 15. The latter [signal memory and transducer 30] electronically produces individual images in the CCIR-standard which are represented on the outlet-connected television monitor 31. On television monitor 31, contrast and luminousity are adjustable as free parameters by means of regulating devices 32 and 33, and they are controllable on the basis of the gray scale 34. Connected in parallel herewith is the apparatus for gradation compensation (screen/film) 35 for the following individual image-recording apparatus 36, which produces the paper image 37 on which the gray scale 38 is visible.

Corresponding to the inventive method of operating the abovedescribed system, the gray scale signal is delivered from the standard-signal generator 6 to the monitor 11 in the primary region I and to the television monitors 19 and 31 in the secondary region II prior to the build-up of the actual ultrasonic image (with switch 1a open). The individual gray scale signals are now capable of being directly objectively compared with one another. By adjusting (or balancing) the regulating devices 12 and 13, 20 and 21, 30 and 32, of monitors 11, 19 and 31, to optimum brightness and contrast by means of the gray scale-standard, an objectively definable coupling of the individual monitors is achieved. The operator can then (after closing switch 1a) build up the ultrasonic image on apparatus 1 by adjustment of the regulating devices 2 through 4 for the purpose of image signal processing. Subsequent to this, additional adjustments on monitors 11, 19, and 31, are generally no longer necessary. The standard-signal generator 6 can be switched off during further operation by means of switch 6a and can be only sequentially switched on for control purposes. Long-term fluctuations due to changes in the external operating conditions or due to drift of individual apparatus can then be followed on the monitors by means of the gray scales 14, 22, and 34, and, if necessary, corrected.

In the case of image recording apparatus 25 and 36 for film and paper, the free parameters, brightness and contrast, are adjustable through suitable selection of film material, exposure, and development. This is first checked on the basis of test photographs, whereby objective coordination again proceeds by means of the gray scale represented on the film or the paper image. During operation of the transmission chain, image recording (or photographic) apparatus 25 and 36 represent closed systems and require no further adjustments.

The signal stored on the magnetic tape by means of video recorder 28 likewise carries the gray scale signal in addition to the image information. During reproduction of such magnetic tape, television monitor 19 is adjusted to correspond to this gray value signal.

The sample embodiment of the invention described in the foregoing consists in its secondary region II of discrete individual sections having a defined linear contrast range which is matched to one another. Thus, there is connected before each optical image recording apparatus an apparatus for gradation compensation which directly compensates the gradation error brought about by image conversion. Consequently, the individual sections can be randomly combined with one another, whereby the constant coupling of the image-contents with the gray scale standard and hence the unequivocal reproducibility of the image-contents is always maintained.

It will be apparent that many modifications and variations may be effected without departing from the scope of the novel concepts and teachings of the present invention.

I claim as my invention:

1. A method for the buildup of ultrasonic images which are obtained on the basis of scanning of a subject by means of ultrasonic waves, and for converting these images, arriving as a sequence of ultrasonic echoes, into an optical visual image; and utilizing:

an ultrasonic image signal processing apparatus which radiates ultrasonic impulses into the subject to be examined and which again receives the ultrasonic echoes reflected in the subject and converts them into ultrasonic image representing electric signals, the ultrasonic image signal processing apparatus including adjustment means for the purpose of adjusting parameters with regard to radiated or received ultrasonic waves, respectively; and an optical reproduction apparatus for the purpose of reproducing the ultrasonic echoes in the form of an optical visual image; and an ultrasonic image signal transmission path for the ultrasonic image representing electric signals; characterized by the following method steps:

(a) mixing into the ultrasonic image signal transmission path between the ultrasonic image signal processing apparatus and the optical reproduction apparatus a gray-scale signal, and as a first step adjusting all brightness and contrast controls affecting the image display by the optical reproduction apparatus to be viewed by the operator of the ultrasonic image signal processing apparatus during reference to the display of the gray-scale signal as a gray-scale representation on the optical reproduction apparatus, so as to optimize such optical reproduction apparatus for medical diagnosis of an ultrasonic image;

(b) transmitting via said ultrasonic image signal transmission path the ultrasonic image representing signals supplied by the ultrasonic image signal processing apparatus to said optical reproduction apparatus for display of an optical visual image in accordance with the sequence of ultrasonic echoes reflected in the subject on the optical reproduction apparatus; and mixing into the ultrasonic image signal transmission path, concurrently with the transmission of the ultrasonic image representing signals thereby, the gray-scale signal so that the gray-scale representation is displayed on the optical reproduction apparatus along with the display of the optical visual image in accordance with the sequence of ultrasonic echoes; and (c) during display of the sequence of ultrasonic echoes and the gray-scale representation according to step (b), and after completion of all brightness and contrast adjustments, as specified in step (a), adjusting the ultrasonic image signal processing apparatus as to ultrasonic parameters including depth compensation and dynamic compression by means of said adjustment means in such a fashion that there results on the optical reproduction apparatus a correspondingly adjusted optical visual image while the optical reproduction apparatus remains adjusted with reference to the display of said gray-scale representation.

2. A method according to claim 1 which comprises transmitting via said ultrasonic image signal transmission path the ultrasonic image representing signals both to a primary optical reproduction apparatus in a primary region at the ultrasonic image signal processing apparatus and to secondary optical reproduction apparatus in a secondary region relatively remote from said primary region, the method further comprising a first method step of adjusting the primary and secondary reproduction apparatus (11, 19, 31) to optimum reproduction properties of contrast and gradation with a set of regulating devices (12, 13; 20, 21; 32, 33), while displaying a gray-scale representation on each such reproduction apparatus, and then, as a second method step, building up the optical visual image to be diagnostically interpreted with the use of adjustment means (2, 3, 4) of the ultrasonic image signal processing apparatus (1) while referring to the primary optical reproduction apparatus (11) which thereby functions as control apparatus for the operator of the ultrasonic image signal processing apparatus.

3. A method according to claim 1 with the mixing into the ultrasonic image signal transmission path being carried out by supplying the ultrasonic image representing signals and the gray-scale signal to respective inputs of a signal mixer (8), and supplying the combined ultrasonic image representing signals and the gray-scale signal to a common input of the optical reproduction apparatus.

4. A method according to claim 3 characterized in that the gray-scale signal is produced by a standard-signal generator (6) which is connected with one of the inputs of the signal mixer (8) and producing by means of the standard-signal generator a gray-scale signal with a defined black-white-gradation as the gray-scale signal for said ultrasonic image signal transmission path at the output of the signal mixer.

5. A method according to claim 2 wherein after building up the optical visual image in accordance with the sequence of ultrasonic echoes with the use of adjustment means (2, 3, 4) of the ultrasonic image signal processing apparatus (1), the gray-scale signal is switched off during further operation.

6. A method according to claim 2 with the further steps of operating the primary reproduction apparatus (11) at a line rate corresponding to the rate of production of ultrasonic impulses, and operating a secondary optical reproduction apparatus (19) at a different line rate different from the rate of ultrasonic impulses produced by the ultrasonic image signal processing apparatus (1), and interposing into the ultrasonic image signal transmission path between the primary and secondary optical reproduction apparatus a standards converter (17) for converting the ultrasonic image representing electrical signals for display by said further reproduction apparatus.

* * * * *